United States Patent
Toda et al.

(10) Patent No.: US 8,604,672 B2
(45) Date of Patent: *Dec. 10, 2013

(54) MULTILAYER ACOUSTIC IMPEDANCE CONVERTER FOR ULTRASONIC TRANSDUCERS

(75) Inventors: Minoru Toda, Lawrenceville, NJ (US); Mitchell L. Thompson, Exton, PA (US)

(73) Assignee: Measurement Specialties, Inc., Hampton, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/609,946

(22) Filed: Sep. 11, 2012

(65) Prior Publication Data
US 2013/0002094 A1    Jan. 3, 2013

Related U.S. Application Data

(62) Division of application No. 12/836,071, filed on Jul. 14, 2010, now Pat. No. 8,264,126.

(60) Provisional application No. 61/238,816, filed on Sep. 1, 2009.

(51) Int. Cl.
*B06B 1/06* (2006.01)

(52) U.S. Cl.
CPC .................................. *B06B 1/0622* (2013.01)
USPC .......................................................... 310/334

(58) Field of Classification Search
CPC ...................................... B06B 1/0622
USPC ......................................... 310/322, 334, 335
See application file for complete search history.

(56) References Cited

U.S. PATENT DOCUMENTS

| | | |
|---|---|---|
| 4,211,948 A | 7/1980 | Smith et al. |
| 4,383,194 A | 5/1983 | Ohigashi et al. |
| 4,507,582 A | 3/1985 | Glenn |
| 4,603,276 A | 7/1986 | Coursant |
| 4,672,591 A | 6/1987 | Breimesser et al. |
| 4,712,037 A | 12/1987 | Verbeek et al. |
| 4,771,205 A * | 9/1988 | Mequio .................. 310/334 |
| 4,976,150 A | 12/1990 | Deka |

(Continued)

FOREIGN PATENT DOCUMENTS

WO    WO2008/056611    * 5/2008 ............... A61B 8/00

OTHER PUBLICATIONS

International Search Report dated Oct. 26, 2013 for related application No. PCT/US2010/046035.

*Primary Examiner* — Derek Rosenau
(74) *Attorney, Agent, or Firm* — Howard IP Law Group, PC

(57) ABSTRACT

An impedance conversion layer useful for medical imaging ultrasonic transducers comprises a low impedance polymer layer and a high impedance metal layer. These layers are combined with corresponding thicknesses adapted to provide a function of converting from a specific high impedance to specific low impedance, wherein the polymer layer is at the high impedance side and the metal layer is at the low impedance side. The effective acoustic impedance of the polymer and metal layer combination may be adapted to configure an impedance converter in the same way as a quarter wavelength impedance converter, converting from low impedance to high impedance (metal to polymer) or from a high impedance to low impedance (polymer to metal). This structure may be used for front matching with the propagation medium and back matching with an absorber for ultrasonic transducers.

20 Claims, 8 Drawing Sheets

(56) References Cited

U.S. PATENT DOCUMENTS

| | | | |
|---|---|---|---|
| 6,160,340 A * | 12/2000 | Guo et al. ............... 310/334 |
| 6,307,302 B1 | 10/2001 | Toda | |
| 6,548,942 B1 | 4/2003 | Panasik | |
| 6,772,490 B2 | 8/2004 | Toda | |
| 6,989,625 B2 | 1/2006 | Suzuki et al. | |
| 2002/0027400 A1 | 3/2002 | Toda | |
| 2004/0174095 A1 | 9/2004 | Bhardwaj | |
| 2005/0001517 A1 | 1/2005 | Yogeswaren | |
| 2005/0046311 A1 | 3/2005 | Baumgartner et al. | |
| 2005/0099097 A1 | 5/2005 | Baumgartner et al. | |
| 2005/0127793 A1 | 6/2005 | Baumgartner et al. | |
| 2005/0194865 A1 | 9/2005 | Angelsen et al. | |
| 2005/0225211 A1 | 10/2005 | Oliver | |
| 2007/0200460 A1 | 8/2007 | Scott | |
| 2007/0222339 A1 * | 9/2007 | Lukacs et al. ............... 310/335 |
| 2008/0007142 A1 | 1/2008 | Toda | |
| 2009/0034370 A1 | 2/2009 | Guo | |
| 2009/0072668 A1 | 3/2009 | Gelly et al. | |
| 2009/0147627 A1 | 6/2009 | Toda et al. | |
| 2010/0066207 A1 * | 3/2010 | Saito ............... 310/335 |

\* cited by examiner

MULTILAYER ACOUSTIC IMPEDANCE CONVERTER FOR ULTRASONIC TRANSDUCERS

CROSS-REFERENCE TO RELATED APPLICATIONS

The present application claims the benefit of and is a continuation of co-pending U.S. patent application Ser. No. 12/836,071, filed Jul. 14, 2010, and claims benefit of U.S. Provisional Patent Application Ser. No. 61/238,816, filed Sep. 1, 2009, which applications are incorporated by reference herein in their entireties for all purposes.

FIELD OF THE INVENTION

The present invention generally relates to acoustic impedance converters for an ultrasonic transducer and methods for designing the same.

BACKGROUND OF THE INVENTION

Ultrasonic transducers are often used as impulse mode transducers operating over a wide range of frequencies. Since such transducers need to handle wideband frequency signals, wideband design is an important subject. In the prior art, impedance converters have been placed on a face of a piezoelectric layer of an ultrasonic transducer to improve the wideband frequency response of the transducer. One of the important applications of wideband transducers is in medical imaging systems. Economical, reliable and reproducible mass-production processes for transducers for use in medical imaging systems are particularly desirable.

Impedance converters for ultrasonic transducers are known in the art. As is known in the art, an ultrasonic transducer includes a piezoelectric active layer, one or more front matching layers on a front face of the piezoelectric active layer to serve as an impedance converter, and a backing absorber on a rear face of the piezoelectric active layer. A typical piezoelectric material, such as lead zirconate titanate (also known as "PZT") has high characteristic acoustic impedance, for example, $Z_{PZT}=30\times10^6$ kg/m²s (Rayl). A typical propagation medium, such as water, has low characteristic acoustic impedance, for example, $Z_R=1.5\times10^6$ Rayl. Because of the difference in characteristic acoustic impedances of these media, acoustic waves in the piezoelectric active layer of an ultrasonic transducer are reflected backward into the piezoelectric active layer at the boundary between the piezoelectric active layer and the transmission medium (the front boundary) and reflected frontward into the piezoelectric active layer at the back boundary (the boundary between the rear face of the piezoelectric active layer and the material to the rear of the piezoelectric active layer). This results in a resonance at a specific frequency in the ultrasonic transducer, as determined by the half wavelength condition of the piezoelectric material.

When such a resonated transducer is driven by a voltage pulse (when acting as a transmitter) or by an acoustic pulse (when acting as a receiver), the signal wave does not decay quickly (a phenomenon known as ringing). This effectively renders such a transducer unsuitable for imaging systems, in which systems short acoustic pulse beams are excited, directionally scanned and reflected back from a target to enable an image of the target to be constructed. A front impedance conversion layer (also known in the art as a matching layer for reducing reflections) is inserted between the front face of the piezoelectric layer and the propagation medium to mitigate creation of resonance due to the difference in the characteristic acoustic impedances of the piezoelectric material and the front propagation medium.

A piezoelectric layer's vibration excites an acoustic wave in the backward direction, i.e., in a direction away from the front face of the piezoelectric layer. A certain amount of reflection from the back boundary towards the front face may be desirable to improve the sensitivity of the ultrasonic transducer. Often a backing absorber layer of acoustic absorber material is attached to the rear face of the piezoelectric layer. If the characteristic acoustic impedance of the backing absorber material effectively matches that of the piezoelectric material, a significant amount of acoustic wave energy passes through the back boundary without reflection and is absorbed by the backing absorber layer. In such a case, the sensitivity of the transducer is lowered and the bandwidth may become excessive for some applications. Therefore, some mismatch between the characteristic acoustic impedance of the piezoelectric material and the backing absorber material is desirable, depending on the required bandwidth and sensitivity.

The characteristic acoustic impedance of the backing absorber material may be selected to obtain a desired performance of the ultrasonic transducer. If a transducer cannot be provided with a backing absorber material of a suitable characteristic acoustic impedance, a back impedance conversion layer may be added between the piezoelectric active layer and the backing absorber layer to provide the necessary overall acoustic impedance at the back boundary of the piezoelectric layer.

A typical acoustic impedance conversion structure may be a layer of uniform thickness, the thickness equal to about one-quarter of the wavelength of a desired operating wavelength of the acoustic transducer. The acoustic impedance conversion layer has a characteristic acoustic impedance ($Z_m$), which is approximately the geometric mean of the characteristic acoustic impedance ($Z_1$) of the propagation medium and the characteristic acoustic impedance ($Z_p$) of the piezoelectric active layer, i.e., $Z_m=\sqrt{(Z_1 \cdot Z_p)}$. Since $Z_1$ is small ($Z_1=Z_R=1.5\times10^6$ Rayl), and the characteristic acoustic impedance of the piezoelectric layer is relatively high, the characteristic acoustic impedance $Z_m$ of the matching layer is selected to be between those of the propagation medium and the piezoelectric layer, i.e., $Z_p>Z_m>Z_1$.

One problem associated with a conventional ultrasonic acoustic impedance conversion layer (i.e., quarter wavelength layer) is the difficulty in choosing a material to obtain an appropriate characteristic acoustic impedance $Z_m$ for both front and back acoustic impedance conversion layers. More specifically, ultrasonic transducers are often required to operate over a wide bandwidth (for example, 40-60% of the center frequency). To obtain satisfactory performance over such a wide bandwidth using bulk PZT as the piezoelectric active layer, a typical acoustic impedance conversion layer structure used comprises a single front matching layer having a characteristic acoustic impedance of $Z_m=6.7\times10^6$ kg/m²s (Rayl).

Another known acoustic impedance conversion structure providing still wider bandwidth uses double matching layers. Here, two quarter wavelength layers having characteristic acoustic impedance of $Z_{m1}$ and $Z_{m2}$ are used. In a structure employing double matching layers, the matching layer with characteristic acoustic impedance $Z_{m1}$ is in contact with the propagation medium, which has a characteristic acoustic impedance $Z_1$; the matching layer with characteristic acoustic impedance $Z_{m2}$ contacts the surface of the piezoelectric layer. The materials of the matching layers are chosen to satisfy a specific relation such as $Z_p>Z_{m2}>Z_{m1}>Z_1$. However, it is quite difficult to obtain appropriate materials for these layers while satisfying the specific designed values of the characteristic acoustic impedances. For example, polyimide has a characteristic acoustic impedance of $3.16\times10^6$ Rayl. Polyester has a characteristic acoustic impedance of $3.4\times10^6$ Rayl, PVDF: $3.7\times10^6$ Rayl, glass: $13.2\times10^6$ Rayl, and aluminum: $17.3\times10^6$ Rayl. In addition to choosing a material for the front matching layer having a suitable characteristic acoustic impedance, the material should desirably meet other criteria such as process compatibility, ease of mass-production, and material cost. In the prior art, epoxy loaded with high characteristic acoustic impedance material such as glass fiber or silica powder has been used. However, the thickness and uniformity of such a loaded epoxy proves difficult to control.

Another problem associated with the conventional design of ultrasonic transducers arises in array transducers, where a flexible printed circuit layer or board on which multiple conductor traces are formed is disposed to the rear of the array. Each conductor trace is connected to one element of the array. A backing absorber is then attached on the rear face of the flexible printed circuit board. The acoustic performance of the flexible printed circuit negatively affects the performance of the transducer. The polymer layer of a typical flexible printed circuit board has characteristic acoustic impedance of about $3.2\times10^6$ Rayl, which is too low and renders the structure insufficient to serve as an adequate matching layer.

When a piezoelectric layer is diced to define an array of elongated elements of narrow width, the kerfs or channels between the elements are filled by a filler material (such as epoxy). As a result, the characteristic acoustic impedance of the piezoelectric layer is reduced. In ultrasonic transducers employing such arrays, the properties of suitable acoustic impedance converters are different from the properties of acoustic impedance converters suitable for transducers having solid piezoelectric active layers. The selection of suitable materials for the acoustic impedance converters is also dependent on bandwidth and sensitivity requirements. Adjusting the characteristic acoustic impedance $Z_m$ of acoustic impedance converters using available techniques has proven difficult.

In ultrasonic transducers with no backing absorber, or with air or a very low characteristic acoustic impedance material as a backing absorber, strong reflections from the back boundary causes the transducer to operate with a relatively narrow resonance, or results in a strong resonance peak. In such ultrasonic transducers, the fabrication of an appropriate acoustic impedance converter for the front face may require high quality workmanship and custom materials. When an acoustic impedance converter for the front face of the piezoelectric layer is properly designed and fabricated, a broadband and high efficiency transducer can be produced. However, large scale production of such transducers is difficult to attain due at least in part to the need for skilled artisans having high quality workmanship and custom materials to create such acoustic impedance converters.

The concept of a multilayer acoustic impedance converter having a low characteristic acoustic impedance layer arranged closer to a piezoelectric layer and a high characteristic acoustic impedance layer bonded at the outer surface of the low acoustic impedance layer is also known in the art. In the prior art, both layers are less than one quarter of a wavelength thick. The combined structure provides an effective acoustic impedance conversion equivalent to that of a quarter wavelength scheme. U.S. Pat. No. 6,772,490 teaches multilayer acoustic impedance conversion layers with such a combination of lower and higher characteristic acoustic impedance layers. The effective characteristic acoustic impedance of the multilayer impedance converter of the '490 patent is lower than the characteristic acoustic impedance of the radiation or propagation medium for achieving high sensitivity when operating the transducer at the center resonant frequency. While this design is suitable for effective energy transfer at the center frequency of a narrow bandwidth (which is often suitable for continuous wave excitation) this design exhibits a steep drop in performance as the frequency is changed away from the center frequency. Such design is unsuitable for operating the transducer at broader bandwidths required for applications such as pulse excitation and reception.

Another example of a prior art transducer arrangement is provided in Toda, "New Type of Matching Layer for Air-Coupled Ultrasonic Transducers," IEEE Transactions on Ultrasonics, Ferroelectrics and Frequency Control, vol. 49, no. 7, July 2002, pp 972-979, which describes a basic design principle of a multilayer acoustic impedance converter for reducing reflection at the front of a piezoelectric layer of a transducer with wideband performance. This is an air acoustic wave transducer. Here, a lower characteristic acoustic impedance layer (formed of air) is disposed at a first surface of the piezoelectric layer and is followed by a higher characteristic acoustic impedance layer (formed of a polymer) contacting the propagation medium of air. Each of these layers is thinner than one quarter wavelength and the combination of these two layers functions as a quarter wavelength impedance converter. For an ultrasonic transducer with water or the human body as the propagation medium having broad bandwidth operation as required for pulse excitation and reception, alternative materials and methods of implementing such transducers are desired.

SUMMARY OF THE INVENTION

According to an embodiment of the present invention, an ultrasonic transducer comprises a piezoelectric element having a characteristic acoustic impedance and a front acoustic impedance converter coupled to the piezoelectric element. The front acoustic impedance converter comprises a front polymer layer having a thickness $t_{p1}$ coupled to the piezoelectric element; and a front metal layer for transmitting acoustic energy between the front polymer layer and a propagation medium having a characteristic acoustic impedance. The front metal layer has a thickness $t_{m1}$ and is coupled to the front polymer layer. The characteristic acoustic impedance of the propagation medium is lower than the characteristic acoustic impedance of the piezoelectric element, and the front acoustic impedance converter has an effective characteristic acoustic impedance $Z_C$ between the piezoelectric element and the propagation medium characteristic acoustic impedances. Transmitting of acoustic energy between the front polymer layer and the propagation medium may take the form of the ultrasonic transducer operating as a transmitter, a receiver, or a transceiver.

In an embodiment of the invention, the thicknesses of the polymer layer and the metal layer are selected so as to provide the impedance converter with the effective characteristic acoustic impedance $Z_{C1}$ based on the densities of the front metal and front polymer layer, the effective characteristic acoustic impedance $Z_{C1}$, a center resonant frequency of the ultrasonic transducer and the velocity of sound in the front polymer layer. According to another embodiment of the invention, the ultrasonic transducer further includes a backing absorber coupled to the piezoelectric element, wherein the backing absorber has an associated characteristic acoustic impedance.

According to yet another embodiment of the invention, the ultrasonic transducer further includes a back impedance converter, interposed between the backing absorber and the piezoelectric element, wherein the multilayer back impedance converter has a characteristic acoustic impedance between the characteristic acoustic impedances of the piezoelectric element and the backing absorber.

According to yet another embodiment of the invention, the ultrasonic transducer further includes a quarter wavelength matching layer in contact with and disposed between the propagation medium and the front acoustic impedance converter. The piezoelectric layer may have an air backing with this design of a double matching structure to provide sufficiently wide bandwidth for certain applications.

Thus, according to an aspect of the invention, a transducer arrangement having an impedance converter that is substantially thinner than one quarter wavelength is compensated for by means of a material layer having a relatively higher impedance (or higher density material) positioned on the lower impedance side (propagation medium side) of the converter. In this manner, the material layer compensates for otherwise degraded converter performance and operates to provide or recover substantially the original impedance conversion function. The higher impedance material layer may comprise a metal layer positioned between the thickness reduced converter layer comprising a polymer layer and the lower impedance region adapted to be converted to a higher impedance.

An impedance conversion layer useful for medical imaging ultrasonic transducers comprises a low impedance polymer layer and a high impedance metal layer. These layers are combined with corresponding thicknesses adapted to provide a function of converting from a specific high impedance to specific low impedance, wherein the polymer layer is at the high impedance side and the metal layer is at the low impedance side. The effective acoustic impedance of the polymer and metal layer combination may be adapted to configure an impedance converter in the same way as a quarter wavelength impedance converter, converting from low impedance to high impedance (metal to polymer) or from a high impedance to low impedance (polymer to metal). This structure may be used for front matching with the propagation medium and back matching with an absorber for ultrasonic transducers.

BRIEF DESCRIPTION OF THE FIGURES

Understanding of the present invention will be facilitated by consideration of the following detailed description of the preferred embodiments of the present invention taken in conjunction with the accompanying drawings, in which like numerals refer to like parts and in which.

DETAILED DESCRIPTION OF THE DRAWINGS

Figure 1A:
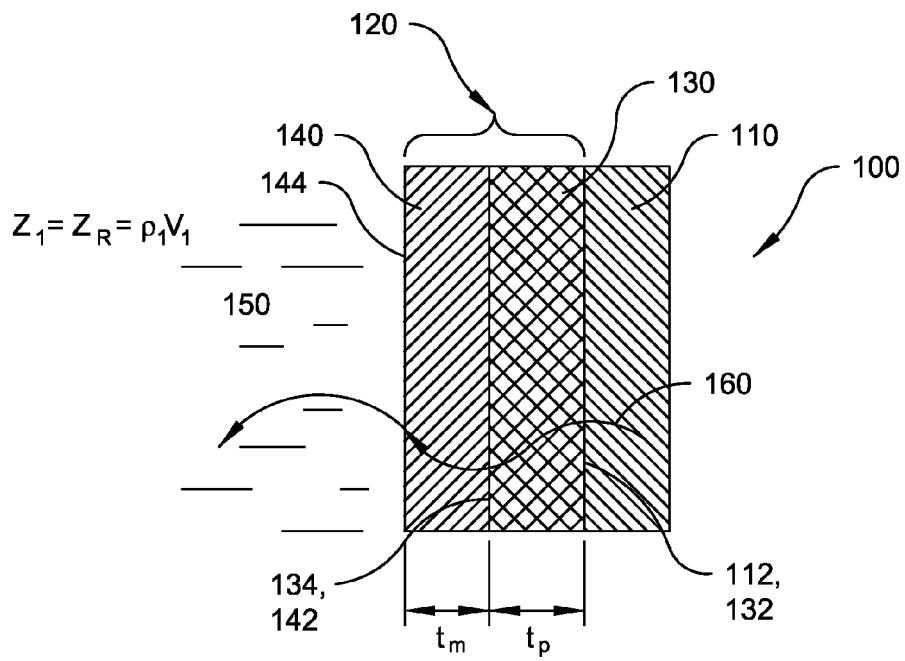
FIG. 1A is a metal polymer multilayer impedance converter for ultrasonic transducers, according to an embodiment of the invention.

Reference will now be made to various embodiments of the invention, examples of which are illustrated in the accompanying drawings. Wherever possible, the same reference numbers will be used throughout the drawings to refer to the same or like parts. It is to be understood that the figures and descriptions of the present invention have been simplified to illustrate elements that are relevant for a clear understanding of the present invention, while eliminating, for purposes of clarity, many other elements found in typical ultrasonic transducers. Because such elements are well known in the art, and because they do not facilitate a better understanding of the present invention, a discussion of such elements is not provided herein. The disclosure herein is directed to all such variations and modifications known to those skilled in the art.

In prior art ultrasonic transducers, a layer of low characteristic impedance material, with a thickness of one quarter of the wavelength of the center frequency of the transducer, is provided between the piezoelectric element and a propagation medium. Exemplary low characteristic impedance materials for air ultrasonic transducers include aerogels and plastic foams. For imaging transducers such as those useful in medical applications, such low characteristic impedance materials include substantially pure polymer and/or polymer loaded with powder and/or fibers. The use of a layer of low characteristic impedance material, referred to as a matching layer or an impedance converter, improves the conversion ratio of electric to acoustic energy in transmitting of acoustic signals, as well as preventing or reducing undesirable phase shift, compared to ultrasonic transducers with no matching layer. However, such matching layers have disadvantages, including an undesirably large thickness for some applications. In addition, if the thickness of the matching layer varies from one quarter of a wavelength of the acoustic wave, the conversion ratio decreases, resulting in observable phase shifts. A matching layer thus is generally undesirable in transducers where broadband or wideband performance (e.g., consistent performance over a wide band of acoustic wavelengths) is required. For example, pulse excitation and reception, often employed in medical ultrasonic imaging, requires good broadband performance. Moreover, as suitable materials are not single phase, scattering of acoustic energy occurs, resulting in undesirable propagation loss. Still further, it is difficult to manufacture suitable materials to obtain specific desired characteristic acoustic impedances, resulting in problems relating to mass production of such transducers for specific applications.

At least some of the drawbacks associated with prior art transducers are addressed in an embodiment wherein a transducer includes a piezoelectric element and a polymer layer disposed on the piezoelectric element. A metal layer is disposed on the polymer layer. The polymer layer and the metal layer together constitute an impedance converter. The thicknesses of the polymer layer and the metal layer are so selected as to provide the impedance converter with an effective characteristic acoustic impedance intermediate the characteristic acoustic impedances of the piezoelectric element and of the propagation medium. Advantageously, by selecting the thicknesses of the metal and polymer layer, a range of effective characteristic acoustic impedances is available. The thickness of this impedance converter may be configured to be much less than one quarter of the wavelength of the target frequency of the acoustic signals.

According to an aspect of the invention, the condition wherein the impedance converter is substantially thinner than one quarter wavelength is compensated for by means of an additional material layer having a relatively higher impedance (or higher density material) positioned on the lower impedance side (propagation medium side) of the converter. In this manner, the additional layer compensates for otherwise degraded converter performance and operates to provide (i.e. recovers) substantially the original impedance conversion function. The higher impedance material layer (e.g. metal layer) is positioned between the thickness reduced converter layer (e.g. polymer layer) and the lower impedance region adapted to be converted to a higher impedance.

The ratio of thicknesses of the metal layer and the polymer layer may be determined based on a predetermined center resonant frequency of the transducer and material parameters. By adapting the thicknesses of both layers to be thinner than one quarter wavelength in each material, in conjunction with determining the thickness ratio among the layers, the method and apparatus of the present invention provides the function of a quarter wavelength impedance converter. Further, the present invention enables the design of arbitrary conversion ratios according to the selection of thickness ratios for each of the layers and the corresponding layer component materials.

Further, by combining two conventionally available material layers with high and low impedances (e.g. a metal layer and a polymer layer), an arbitrary effective acoustic impedance $Z_m$ is synthesized as described herein, having the same function as that of a quarter wavelength impedance converter with acoustic impedance $Z_m$. The method and apparatus of the present invention thus mitigates the problems associated with obtaining specific values of acoustic impedance $Z_m$ according to conventional quarter wavelength designs.

Advantageously, an impedance converter having a desired characteristic acoustic impedance can readily be fabricated from commercially available metal and polymer materials, thereby facilitating mass production of impedance converters and reducing costs of production compared to prior art matching layers. Good performance over a broadband range around the center resonant frequency may be obtained, so that a transducer with an impedance converter according to the invention is suitable for applications, such as medical imaging, requiring good broadband performance.

Figure 1B:
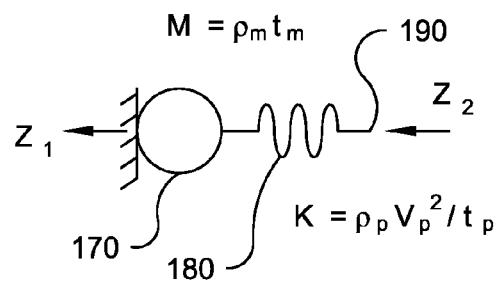
FIG. 1B is a mass and spring model for the metal polymer multilayer impedance converter of FIG. 1A.

Referring now to FIGS. 1A-1B, an ultrasonic transducer 100 with a multilayer acoustic impedance converter 120 is schematically illustrated. Transducer 100 includes a piezoelectric body or element 110 having a high characteristic acoustic impedance $Z_P$ (e.g., 20-30×10⁶ kg/m²s or MRayl). Multilayer acoustic impedance converter 120 includes a polymer layer 130 having a predetermined thickness $t_p$ and a metal layer 140 having a predetermined thickness $t_m$. In an exemplary embodiment, the layers 130, 140 each may be of substantially uniform thickness $t_p$ and $t_m$ respectively. In other configurations, layers 130, 140 may have varying thicknesses $t_p$ and $t_m$ respectively. The effective or equivalent characteristic acoustic impedance $Z_C$ of the combined polymer layer 130 and metal layer 140 is adapted to provide appropriate functionality as an acoustic impedance converter 120. In an exemplary embodiment, polymer layer 130 has parallel opposing planar first surface 132 and second surface 134. Metal layer 140 has parallel opposing planar first surface 142 and second surface 144. In an exemplary configuration, metal layer 140 may be of copper, brass, aluminum, steel or other suitable metal. First surface 132 of polymer layer 130 is bonded or otherwise coupled to piezoelectric body or element 110 of ultrasonic transducer 100. First surface 142 of metal layer 140 is bonded or otherwise coupled (e.g. via electroplating metal onto polymer or via electroless plating) to second surface 134 of polymer layer 130. Second surface 144 of metal layer 140 may be disposed in contact with a propagation medium 150 (for example, water or a biological tissue of an animal, such as a human) having a low characteristic acoustic impedance $Z_R$ (e.g., 1.5 MRayl). It is understood that metal layer 140 may include a thin material coating, for example, a paint coating, having negligible effect on the effective characteristic acoustic impedance of the converter 120, and interposed between metal layer 140 and propagation medium 150. The presence of such a thin layer is also intended to be interpreted as metal layer 140 being in contact with propagation medium 150. Metal layer 140 serves to transmit ultrasonic energy between propagation medium 150 and piezoelectric element 110 through polymer layer 130. The layers 130, 140 may be directly in contact with one another at respective surfaces 134, 142, or may be coupled via a thin adhesive layer disposed therebetween. The thin adhesive layer has no significant effect (i.e. negligible effect) on the effective acoustic impedance of acoustic impedance converter 120.

Still referring to FIG. 1A, an ultrasonic wave 160 originates from piezoelectric element 110 and propagates normal to the surface of polymer layer 130 from piezoelectric element 110 towards metal layer 140 and into propagation medium 150.

The thicknesses $t_m$ and $t_p$ of the metal and polymer layers 140, 130 respectively, may be selected so that the effective characteristic acoustic impedance $Z_C$ of impedance converter 120 is between that of propagation medium 150 (i.e., $Z_R$) and the active piezoelectric element 110 (i.e., $Z_P$).

FIG. 1B illustrates a mass and spring model used to calculate the wave impedance or specific acoustic impedance $Z_2$ of acoustic impedance converter 120 as seen from the surface 132 of polymer layer 130 to metal layer 140. A mass 170 represents metal layer 140 and a spring 180 represents polymer layer 130. Spring 180 has an end point 190. The following calculations and conditions are provided by way of example to illustrate how impedance conversion takes place by means of the polymer and metal layers. Actual values are not limited to the precise values described herein but based on practical requirements for the specific application. For example, certain applications may not require a wide bandwidth, while in other cases, design of bandwidth and sensitivity are achieved as the cumulative effect of each section (e.g. front and back) without satisfying the below criteria. In any event, for calculations of specific acoustic impedance $Z_2$, the mass M of mass 170 is calculated as:

$$M = \rho_m t_m \text{ per unit area,} \qquad (1)$$

wherein
$\rho_m$ is the density of metal layer 140; and
$t_m$ is the thickness of metal layer 140.

Likewise, the spring constant K of spring 180 is calculated as:

$$K = c_{33}/t_p = \rho_p V_p^2 / t_p \quad (2)$$

wherein $c_{33}$ is the stiffness constant in the direction of thickness $t_p$;
$t_p$ is the thickness of polymer layer 130;
$\rho_p$ is the density of polymer layer 130;
$V_p$ is the acoustic velocity in polymer layer 130.

Equation (2) uses the known relationship $V_p = \sqrt{(c_{33}/\rho_p)}$.

In the model above, the mass of polymer layer 130 was neglected. However, a part of polymer layer 130 proximate to metal layer 140 moves with metal layer 140 such that at least a portion of the mass of polymer layer 130 influences the mass of metal layer 140. When metal layer 140 is thinner than polymer layer 130, the mass M of mass 170 may, therefore, be approximated as:

$$M = \rho_m t_m + 0.4(\rho_p t_p) \quad (3)$$

As is known in the art, the resonant frequency $f_o$ of impedance converter 120 may then be calculated as:

$$f_0 = \frac{1}{2\pi}\sqrt{\frac{K}{M}} \quad (4)$$

As described below, the specific acoustic impedance at end point 190 of spring 180 is the highest at a resonance condition. When subjected to an ultrasonic wave 160 (see FIG. 1A), end point 190 displaces to the left in FIG. 1B, i.e., towards mass 170, and spring 180 generates a force pushing mass 170 to the left, at a given start time. Consequently, mass 170 starts to move and is displaced to the left. The displacement of mass 170 is a maximum after one quarter cycle of the resonant frequency, since the displacement of mass 170 lags by one quarter cycle the displacement of the end point 190 of spring 180 and the amplitude of the spring oscillation is greatest at a resonant frequency. At one quarter cycle after the start time, spring 180 elongates to a maximum length and the force from spring 180 is the largest. At this time, end point 190 returns to its original position, and the vibration velocity of end point 190 reaches its maximum in one cycle period as the mass 170 is now moved to the left and exerts force on spring 180.

As is known in the art, the specific acoustic impedance $Z_2$ of impedance converter 120 is given by the force at end point 190 divided by the velocity at that time. Since at a resonant frequency, the force on end point 190 is at a maximum, the specific acoustic impedance $Z_2$ becomes a maximum at the resonant frequency. In an ideal model, without spring losses, the specific acoustic impedance $Z_2$ approaches infinity at the resonant frequency and the resonance is sharp. However, the radiation or propagation medium impedance $Z_1$ is attached to mass 170 and its effect is equivalent to a resistive load. The propagation medium impedance $Z_1$ thereby serves to damp the resonance. As a result, the resonance is broadened. An analysis of mass 170 and spring 180 with radiation or propagation impedance $Z_1$ at mass M provides the specific acoustic or wave impedance $Z_2$, at resonant frequency $f_o$ as seen from end point 190 as:

$$Z_2 = MK/Z_1 \quad (5)$$

wherein, $Z_1 = Z_R = \rho_1 V_1$ is the characteristic acoustic impedance of propagation medium 150 (e.g., about 1.5 MRayl);
$\rho_1$ is the density of propagation medium 150; and
$V_1$ is the acoustic velocity of propagation medium 150.

Thus, using the practical parameters of $Z_1 = Z_R$ and M (i.e., mass per unit area of metal layer 140) and K (i.e., spring force per unit area divided by displacement for polymer layer 130), the specific acoustic impedance $Z_2$ of converter 120 has a much higher value than the radiation or propagation impedance $Z_R$. This acoustic impedance converter 120 having thinned polymer and metal layers, has the same function as the well known quarter wavelength relatively thick matching layer in contact with propagation medium 150. In the conventional quarter wavelength matching layer case, the specific wave impedance of the quarter wavelength layer as seen from the back side is converted to $$Z_2 = Z_m^2/Z_1 \quad (6)$$

wherein, $Z_m$ is the characteristic acoustic impedance of the quarter wavelength matching layer. In the prior art, this quarter wavelength matching layer is bonded to the front surface of a piezoelectric layer (having characteristic acoustic impedance $Z_{PZT} = 30$ MRayl) in an ultrasonic transducer. Impedance $Z_2$ is the wave or specific acoustic impedance seen from the piezoelectric layer. Thus, the propagation medium acoustic impedance $Z_1$ is up-converted to $Z_2$, which is close to $Z_{PZT}$.

As is known in the art, for a piezoelectric material having a high characteristic acoustic impedance $Z_{PZT}$, the specific acoustic impedance $Z_2$ of converter 120 has to be close to $Z_{PZT}$ for an efficient energy transfer between the piezoelectric material and impedance converter 120 and $Z_1 = Z_R$ (i.e., acoustic impedance of propagation medium 150). In an ideal matching condition, if $Z_2 = Z_{PZT}$, $Z_m$ has to be equal to $\sqrt{(Z_{PZT} Z_R)}$. However, as a practical matter, the value of the specific acoustic impedance $Z_2$ of converter 120 need not be identical to the value of the characteristic acoustic impedance $Z_{PZT}$ of the active piezoelectric material. In exemplary embodiments, the specific acoustic impedance $Z_2$ of converter 120 is not significantly different from the value of the characteristic acoustic impedance $Z_{PZT}$ of piezoelectric element 110 and the condition $Z_1 < Z_m < Z_{PZT}$ generally holds true. The value of $Z_m$ is conventionally chosen to be between $Z_1$ and $Z_{PZT}$ depending on the design requirements for the particular application.

Still referring to FIG. 1A in conjunction with FIG. 1B, the thickness $t_m$ of metal layer 140 and the thickness $t_p$ of polymer layer 130 may be calculated as follows. Equation (4) above states:

$$f_0 = \frac{1}{2\pi}\sqrt{\frac{K}{M}}$$

Inserting the values for K and M from Equations (2) and (1) respectively in Equation (4), $$f_0 = \frac{V_p}{2\pi}\sqrt{\frac{\rho_p}{\rho_m t_m t_p}} \quad (7)$$

Further, from Equation (6) above, $$Z_C^2 = Z_1 \cdot Z_2 \quad (8)$$

and from Equation (5) above, $$Z_1 \cdot Z_2 = MK \quad (9)$$

Thus, from Equations (8) and (9), $$Z_C = \sqrt{(MK)} \quad (10)$$

This equation means the value $Z_C$ may be chosen by selecting materials with thicknesses that yield suitable values of M and K. The value $Z_C$ may be called an effective characteristic acoustic impedance of acoustic impedance converter 120 and provides for selection of an effective characteristic acoustic impedance for a multilayer impedance converter. While the structures associated with the aforementioned cases are distinct, the effect of the impedance conversion is the same. The impedance $Z_1$ is converted to $Z_2$ and the multilayer converter structure has its effective acoustic impedance $Z_C$ as $Z_m$. If the conversion ratio $Z_2/Z_1$ is the same for both cases, then $Z_C$ corresponds to $Z_m$, thereby being equivalent in function.

Inserting values of M and K from Equations (1) and (2) respectively into Equation (10), there is obtained $$Z_C = V_p \cdot \sqrt{(\rho_m \cdot \rho_p \cdot t_m/t_p)} \qquad (11)$$

Equations (7) and (11) can be solved for $t_m$ and $t_p$ as follows: Equation (7) is first solved for $V_p$ and the value of $V_p$ is substituted into Equation (11). $t_m$ may then be determined as below:

$$t_m = Z_C/(\rho_m 2\pi f_o) \qquad (12)$$

The thickness $t_m$ of metal layer 140 is linearly dependent on the desired effective characteristic acoustic impedance $Z_C$ of impedance converter 120, and is inversely dependent on the density of the metal of metal layer 140 and the center resonant frequency of transducer 100.

Equations (7) and (11) are solved by eliminating the term $\rho_m t_m$ by making a product of terms of left side of Equations (7) and (11) to get $f_o Z_C$, and by making a product of terms of right side of these two equations to get $V_p^2 \rho_p/t_p$. From equality of the left and right products, we get $t_p$ as below:

$$t_p = V_p^2 \rho_p/(2\pi f_o Z_C) \qquad (13)$$

The thickness $t_p$ of polymer layer 130 is inversely dependent on the center resonant frequency $f_o$ of transducer 100 and the desired effective characteristic acoustic impedance $Z_C$ of impedance converter 120. The thickness $t_p$ of polymer layer 130 is directly linearly dependent on the density of the polymer of polymer layer 130. The thickness $t_p$ of polymer layer 130 is further proportional to the square of the acoustic velocity in the polymer layer 130. Thus, for a given or required $Z_C$ for a given application and a given center resonant frequency $f_o$, thickness $t_m$ of metal layer 140 and thickness $t_p$ of polymer layer 130 may be calculated using Equations (12) and (13). Both thicknesses $t_m$ and $t_p$ are linearly related to the center resonant frequency $f_o$ of transducer 100. The ratio of the thickness $t_m$ of metal layer 140 to the thickness $t_p$ of polymer layer 130 may be expressed as $$t_m/t_p = Z_C^2/(\rho_m V_p^2 \cdot \rho_p) \qquad (14)$$

The thickness ratio is accordingly independent of the center resonant frequency $f_o$ of transducer 100. The ratio of the metal thickness $t_m$ to the polymer thickness $t_p$ increases with the square of the desired effective characteristic acoustic impedance $Z_C$ of impedance converter 120. It will be understood that the values of thicknesses $t_m$ and $t_p$ calculated using Equations (12) and (13) may serve as starting points for the design of acoustic impedance converter 120 and may be varied therefrom without departing from the scope of the invention. The thicknesses $t_m$ and $t_p$ may be varied depending on the commercial availability of the chosen materials of standard thicknesses. These variations in the thicknesses of $t_m$ and $t_p$ from those determined through Equations (12) and (13) are intended to be within the scope of the present invention.

It will be further understood that an acoustic impedance converter may perform satisfactorily even though the thicknesses $t_m$ and $t_p$ may not satisfy Equations (12) and (13). A desired overall performance for an ultrasonic transducer may be achieved with a non-ideal front acoustic impedance converter and a non-ideal back impedance converter, both of which may deviate from the values determined using the method described herein. However, the phase shift resulting from the front and back matching layer(s) may be cancelled by using a higher resonant frequency for the front matching layer(s) and a lower resonant frequency for the back matching layer(s) relative to the center resonant frequency. Yet another example is an ultrasonic transducer with no back matching layer (i.e., with air backing), which may use double front acoustic impedance converters in order to provide a structure with sufficiently wide bandwidth for a given application. In such a transducer each individual acoustic converter may deviate from the ideal values. However, the effective combined characteristic acoustic impedance may provide satisfactory overall performance because of the cancelling effect of the two acoustic impedance converter structures, wherein one of the acoustic impedance converter may be configured for a higher resonant frequency and the other for a lower resonant frequency relative to the center resonant frequency of ultrasonic transducer 100.

Figure 2:
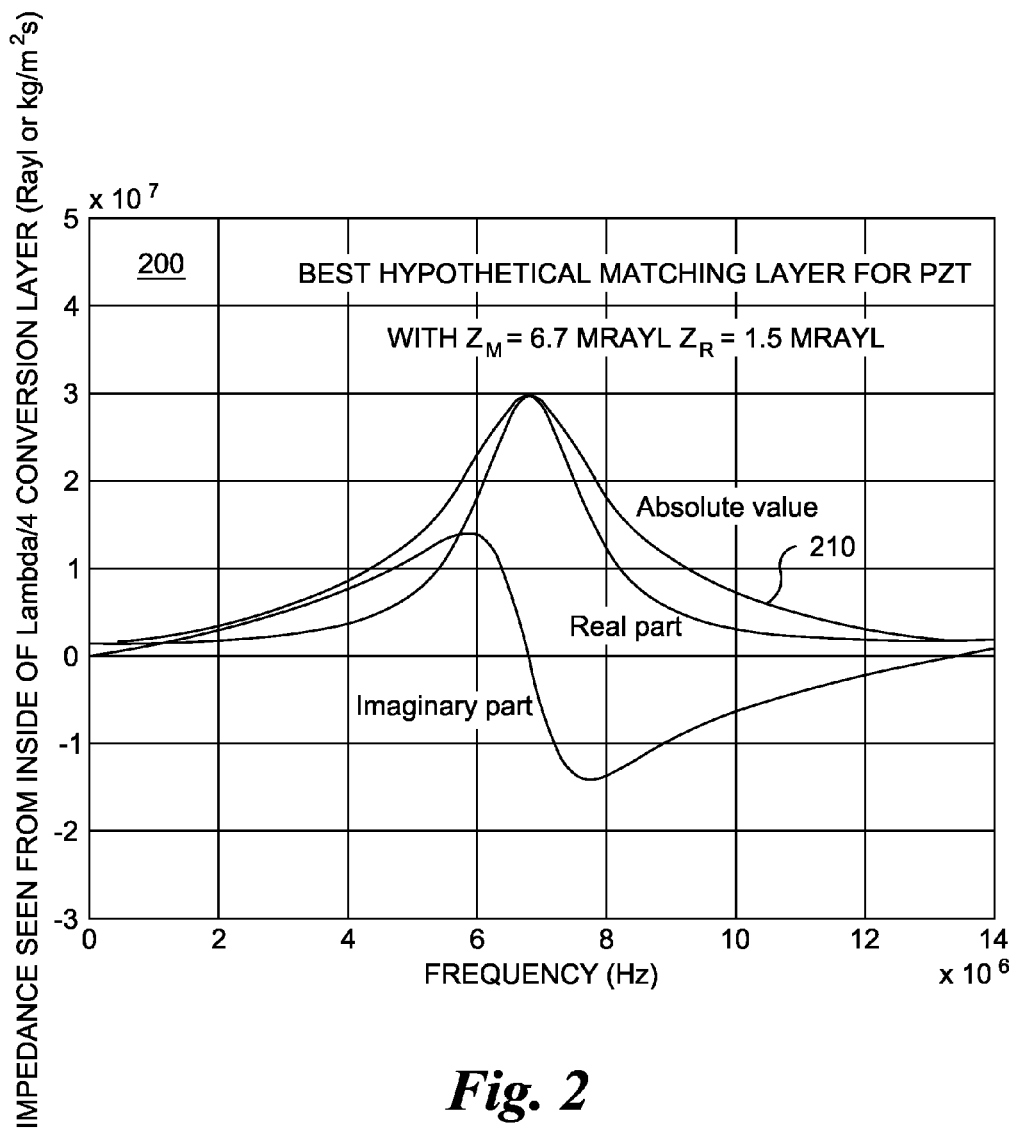
FIG. 2 illustrates the impedance performance of a prior art quarter wavelength matching layer with $Z_R=1.5$ MRayl, loaded with water.

Referring now to FIG. 2, there is illustrated a chart 200 depicting the results of a specific acoustic impedance $Z_2$ calculation using a one dimensional wave propagation model (i.e., not using the mass and spring model), as known in the art, for wave or specific acoustic impedance $Z_2$ of a quarter wavelength matching layer for which the characteristic acoustic impedance has an ideal value of $Z_m = 6.7 \times 10^6$ Rayl and $Z_R = 1.5 \times 10^6$ Rayl for the propagation medium loaded at the front side of the quarter wavelength matching impedance layer of an ultrasonic transducer. The wave impedance 210 seen from the back of the quarter wavelength matching layer shows a peak at 6.8 MHz with a value of specific acoustic impedance $Z_2 = 30 \times 10^6$ Rayl which is equal to the characteristic acoustic impedance of the piezoelectric material, $Z_{PZT}$. However, as set forth above, it is difficult to obtain a material having the desired ideal value of characteristic acoustic impedance $Z_m = 6.7 \times 10^6$ Rayl for fabricating the quarter wavelength matching layer of an ultrasonic transducer.

Figure 3:
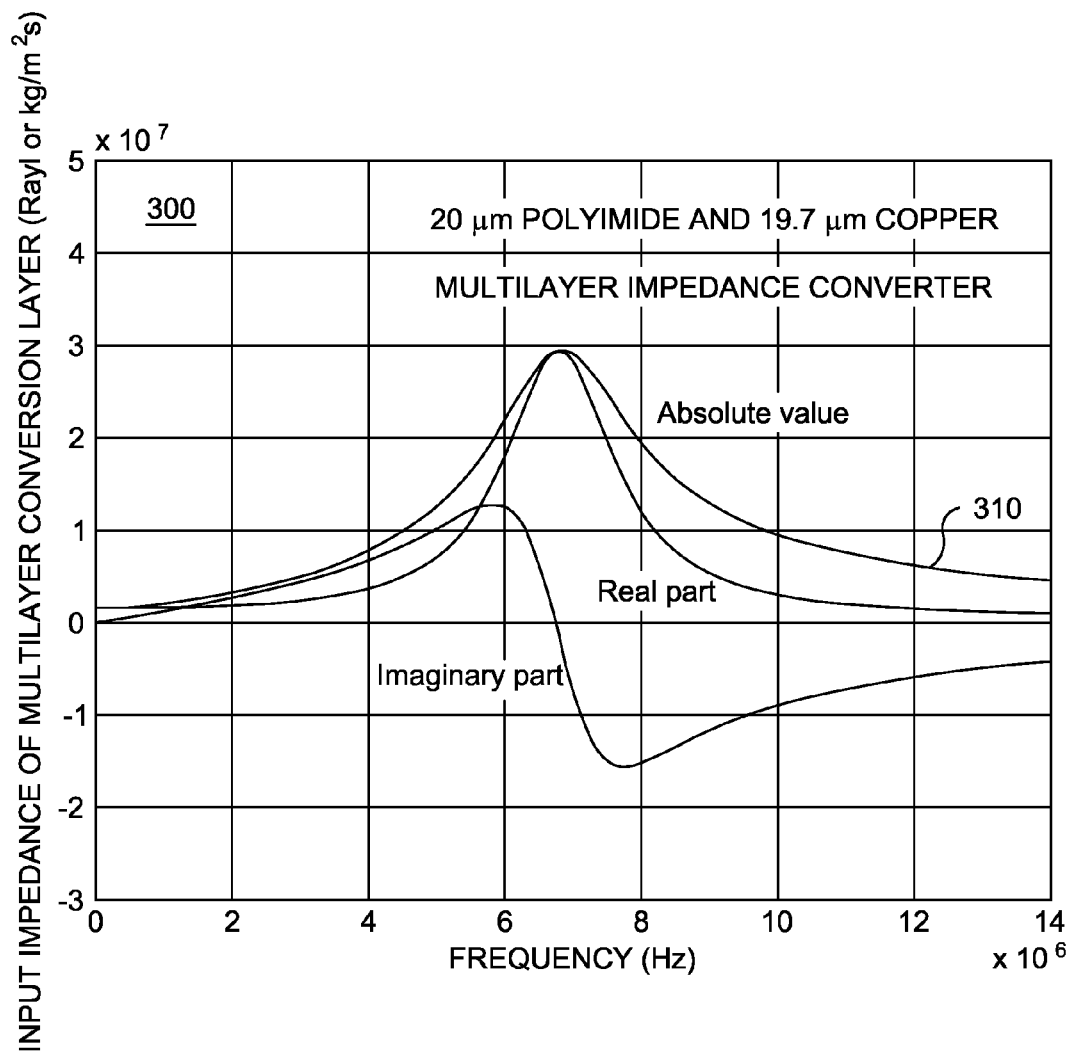
FIG. 3 illustrates the impedance performance of a polyimide/copper multilayer impedance converter designed for 6.8 MHz, according to an embodiment of the invention.

Referring now to FIG. 3, a chart 300 illustrates the specific acoustic impedance $Z_2$ seen from polymer layer 130 to propagation medium 150 for a multilayer impedance converter 120 of FIG. 1A calculated using the same rigorous one dimensional wave propagation model as for FIG. 2. In an exemplary configuration, polymer layer 130 takes the form of a polyimide layer with density $\rho_p = 1454$ kg/m$^3$, sound velocity $V_p = 2175$ m/s and thickness $t_p = 20$ μm (about 1/16 of the wavelength). In this embodiment, metal layer 140 takes the form of a copper layer 12 with density $\rho_m = 8960$ kg/m$^3$, sound velocity $V_m = 5010$ m/s and thickness $t_m = 19.7$ μm (about 1/37 of the wavelength). This exemplary configuration of impedance converter 120 yields specific acoustic impedance $Z_2 = 30$ MRayl at 6.8 MHz peak which ideally matches to characteristic acoustic impedance $Z_{PZT}$ of bulk PZT which typically has $Z_{PZT} = 30$ MRayl. It is further noted here that the quarter wavelength in polyimide layer 130 is 80 μm and the copper layer is 184 μm at 6.8 MHz and, therefore, 20 μm as per the present design is much thinner than a quarter of the wavelength at the center resonant frequency of the piezoelectric active material. It is understood that the design of the same impedance conversion ratio at a different frequency can be accomplished using the same ratio of thickness to wavelength for the same materials.

The impedance curve 310 of impedance converter 120 (of FIG. 1A) shown in FIG. 3 is very close to that of the ideal impedance performance depicted by curve 210 shown in FIG. 2. Thus, selection of suitable thicknesses and material parameters of the polymer 130 and metal 140 layers provides for an arbitrary value of an equivalent characteristic acoustic impedance. It is noted that the thicknesses of each of polymer layer 130 and metal layer 140 are much thinner than the quarter wavelength matching layers of the same materials.

Figure 4:
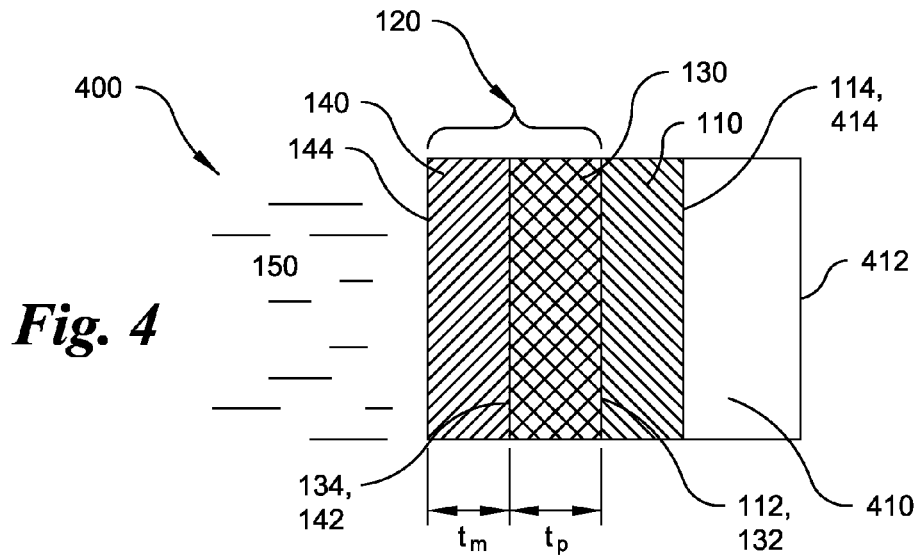
FIG. 4 illustrates an ultrasonic transducer with a polymer-metal multilayer impedance converter, according to an embodiment of the invention.

Referring now to FIG. 4, there is schematically illustrated an ultrasonic transducer 400 configured to operate at high frequency (i.e., in the MHz region) according to an embodiment of the invention. Transducer 400 includes a piezoelectric element 110 having a front acoustic impedance converter 120 bonded to piezoelectric element 110 at a boundary plane 112. A backing absorber 410 is bonded to the piezoelectric element 110 at a boundary plane 114. Impedance converter 120 may be bonded to piezoelectric element 110 using an adhesive such as an epoxy. Boundary plane 114 is opposite to boundary plane 112. Thus, backing absorber 410 is attached to piezoelectric element 110 on a face opposite the face of piezoelectric element 110 on which is attached front impedance converter 120. Front acoustic impedance converter 120 contacts propagation medium 150. It will be understood that front acoustic impedance converter 120 may contact propagation medium 150 through a thin intervening layer, such as a paint coating, having a negligible effect on the effective characteristic acoustic impedance of converter 120.

Generally, piezoelectric element 110 (for example, a piezoelectric ceramic layer) has a high characteristic acoustic impedance $Z_1$ (about 20-30 MRayl depending on the configuration and the material, e.g., $Z_{PZT}$ approximately equal to 30 MRayl)). Propagation medium 150 generally has a relatively low characteristic acoustic impedance $Z_R$ (for example, about 1.5 MRayl). Acoustic impedance converter 120 includes a polymer layer 130 of thickness $t_p$ and a metal layer 140 of thickness $t_m$ bonded to polymer layer 130. The thicknesses $t_m$ and $t_p$ for the metal layer 140 and the polymer layer 130 have been selected based on the desired or predetermined equivalent or effective characteristic acoustic impedance $Z_C$ of acoustic impedance converter 120. An ideal value of specific acoustic impedance $Z_2$, (which, as noted above is close to characteristic acoustic impedance $Z_{PZT}$) determined by the effective characteristic acoustic impedance $Z_C$ can be obtained as shown in FIG. 3. Thus, a wideband transducer can be configured more easily and economically than the prior art systems and methods.

Generally, the vibration of piezoelectric element 110 excites acoustic waves in a forward direction (to the left in FIG. 4) toward propagation medium 150 and also in a rearward direction (to the right in FIG. 4) toward backing absorber 410. Some of the energy of acoustic waves propagating in a rearward direction is transmitted to backing absorber 410. The remainder is reflected at back boundary 414 between piezoelectric element 110 and backing absorber 410. A certain amount of reflection is desirable to enhance the sensitivity of transducer 400 to drive and to receive ultrasonic waves. This reflection at back boundary 414 is a function of the characteristic acoustic impedance of backing absorber 410. If the acoustic absorption in backing absorber 410 is not sufficiently high, ultrasonic waves reflected from an end surface 412 of backing absorber 410 may be reflected back to piezoelectric element 110 and may overlap with a front wave propagating towards propagation medium 150. Disadvantageously, the ultrasonic waves may be destructively or constructively added depending on the frequency, and multiple resonance peaks may be formed on the frequency response curve of transducer 400. Another problem caused by excessively low acoustic absorption by the absorption material of backing absorber 410 is that the thickness of backing absorber 410 has to be increased so as to absorb substantially all backward waves and prevent reflection from end surface 412. If the thickness of backing absorber 410 is excessive, then the transducer 400, with its backing absorber, may not fit within the limitations of the transducer holder or housing, the size of which may be constrained depending on the application of transducer 400.

Figure 5:
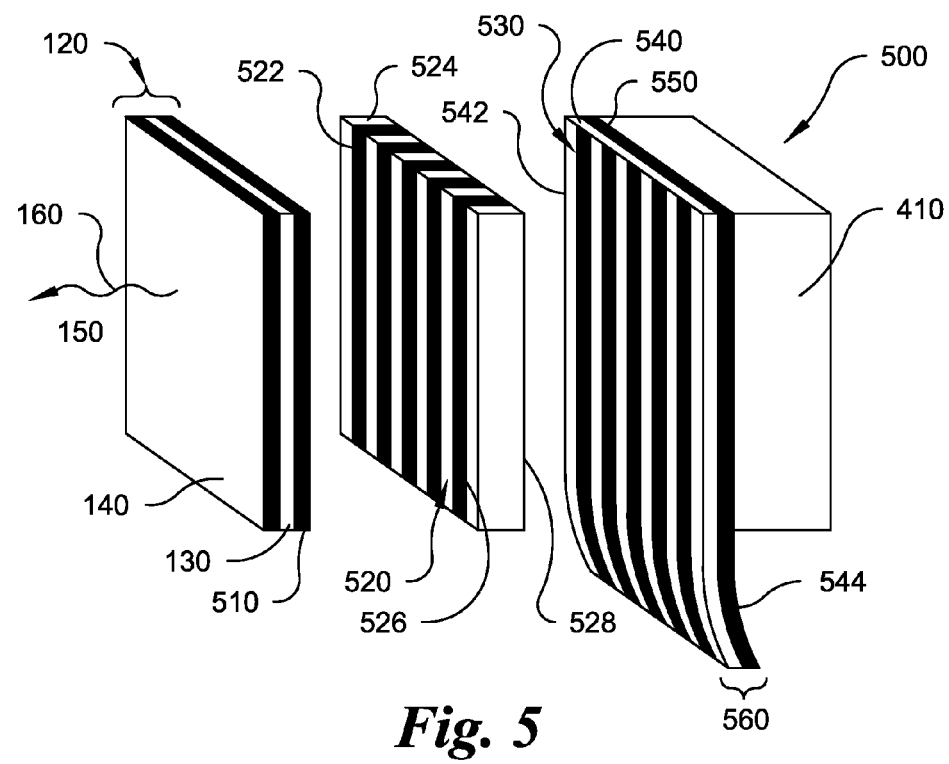
FIG. 5 illustrates an embodiment of an ultrasonic transducer with a multilayer impedance converter on a front face of a piezoelectric layer and a backing absorber layer, according to an embodiment of the invention.

FIG. 5 depicts an ultrasonic transducer 500 having a back impedance converter 560 for backing absorber 410 according to another embodiment of the invention. Generally, characteristic acoustic impedance (MRayl) and acoustic absorption (decibel/centimeter or dB/cm) are closely related and cannot be controlled independently. A material having a high acoustic absorption often has a low characteristic acoustic impedance. The desired characteristic acoustic impedance of a backing absorber 410 may vary depending on the material and structure of the active piezoelectric layer. Examples of the active piezoelectric layer having various desirable characteristic acoustic impedances for backing absorber 410 include bulk PZT, 2-2 composite, 1-3 composite and single crystals.

As shown in the exploded view of FIG. 5, transducer 500 includes a PZT/polymer 2-2 connectivity composite array 520, a front acoustic impedance converter 120 attached (e.g. bonded) to a front surface 526 of array 520 via a grounding layer 510, a flexible printed circuit board 540 with conductor traces 530 (e.g., copper), a shielding conductive layer 550 (e.g. copper) and a backing absorber 410. Backing absorber 410 is attached (e.g. bonded) to a back surface 528 of array 520 through conductive shielding layer 550, flexible circuit board 540 and conductor traces 530. Flexible printed circuit board 540 serves to provide a route for electrical signals and also functions as a back acoustic impedance converter 560 including the polymer of the flexible printed circuit board 540 and the metal of shielding conductive layer 550 to up-convert the low characteristic acoustic impedance of backing absorber 410. Composite array 520 includes multiple narrow elongated elements 524 (for example, about 10 millimeters (mm)×0.1 mm) of PZT with kerfs or channels 522 (for example, of about 50 micrometers (μm) width) therebetween filled with a polymer, such as epoxy. Each piezoelectric element 524 of composite array 520 may be driven with different signals having different phases to steer beam direction. Backside electrodes (not shown) of composite array 520 are connected to conductive traces 530 of flexible printed circuit board 540, along a first surface 542 of flexible printed circuit board 540. The flexible printed circuit board 540 is coupled along a second surface 544 thereof, opposite to first surface 542, to back acoustic impedance converter 560 which, in turn, is coupled to a backing absorber 410. Because of the narrow width geometry of piezoelectric elements 524, the characteristic acoustic impedance $Z_{PZT}$ of piezoelectric elements 524 may be as low as 15 MRayl. In this embodiment, acoustic impedance converter 120 has metal layer 140 of thickness $t_m$=15 μm as a front layer and polymer layer 130 of thickness $t_p$=40 μm on metal layer 140. This exemplary metal-polymer multilayer acoustic impedance converter 120 yields specific acoustic impedance $Z_2$=15 MRayl at 5.2 MHz, which $Z_2$ matches the $Z_{PZT}$ of 2-2 PZT/polymer composite array 520.

In the illustrated embodiment of FIG. 5, polymer layer 130 of acoustic impedance converter 120 may be of polyimide and metal layer 140 may be of copper. The thickness of copper layer 140 may be so selected as to provide an appropriate acoustic impedance conversion from the low characteristic acoustic impedance of propagation medium 150 ($Z_R$) to the high characteristic acoustic impedance $Z_{PZT}$ of PZT/polymer composite array 520. A second copper layer 510 is interposed between acoustic impedance converter 120 and PZT/polymer array 520 as a connection to ground. Copper layer 510, however, does not function as an acoustic impedance converter because layer 510 has a characteristic acoustic impedance similar to that of piezoelectric elements 524 and because layer 510 is directly bonded to piezoelectric elements 524 as a grounded electrode. Therefore, the presence of copper layer 510 does not influence the design of composite or multilayer acoustic impedance converter 120. It will be understood that PZT composite array 520, front matching or acoustic impedance converter 120 and back acoustic impedance converter 560 are shown separately (i.e., not bonded or otherwise coupled) for illustrative purposes only.

To provide backing absorber 410 with an appropriate acoustic impedance conversion, back acoustic impedance converter 560 in FIG. 5 may be provided between piezoelectric array 520 and backing absorber 410. Generally, the characteristic acoustic impedance of backing absorber 410 is about 4-10 MRayl, which is higher than the characteristic acoustic impedance of front propagation medium 150, which may be about 1.5 MRayl, for example. The desired effective acoustic impedance $Z_C$ of back acoustic impedance converter 560 may be selected to be consistent with the desired bandwidth and sensitivity of transducer 500. For example, when the characteristic acoustic impedance of backing absorber 410 is 5 MRayl, and a required specific backing acoustic impedance is 10 MRayl, the desired effective characteristic impedance of the back acoustic impedance converter $Z_C$ ($=\sqrt{(MK)}=\sqrt{(Z_1 \cdot Z_2)}$) is 7.07 MRayl. This value of the effective characteristic acoustic impedance of back acoustic impedance converter 560 is obtained by using a metal (for example, copper) layer 550 with thickness $t_m=24$ μm and a polymer (for example, polyimide) layer 540 with thickness $t_p=29$ μm, for a transducer having a center resonant frequency of 5.2 MHz. The selection of appropriate materials and thicknesses $t_m$, $t_p$ for metal layer 550 and polymer layer 540 for back acoustic impedance converter 560 interposed between an active piezoelectric element 524 and a backing absorber 410 is made in substantially the same manner as for front acoustic impedance converter 120 between active piezoelectric array 520 and front propagation medium 150. Back acoustic impedance converter 560 converts the low characteristic acoustic impedance $Z_1$ of backing absorber 410 to a higher specific acoustic impedance $Z_2$ which is the wave impedance or specific impedance as seen from active piezoelectric array 520 to the interior of backing absorber 410. An appropriate value for specific acoustic impedance $Z_2$ is determined from the desired bandwidth and sensitivity of transducer 500. The desired value of the effective characteristic acoustic impedance, $Z_C$, of back acoustic impedance converter 560 is calculated using the equation $Z_C$=square root of the product of $Z_2$ and $Z_1$ (i.e. $Z_C=\sqrt{(Z_2 \times Z_1)}$). The thickness $t_m$ of metal layer 550 is determined based on the desired effective characteristic acoustic impedance $Z_C$ of back acoustic impedance converter 560, the density of the metal of metal layer 140, and the center resonant frequency $f_o$ of transducer 500. The thickness $t_p$ of polymer layer 540 is calculated based on the desired effective characteristic acoustic impedance $Z_C$ of back acoustic impedance converter 560, the density of the polymer of polymer layer 540, the acoustic velocity in the polymer of polymer layer 540, and the center resonant frequency $f_0$ of transducer 500.

Table I below lists the material parameters for an exemplary propagation medium (water), an exemplary piezoelectric active material (PZT), an exemplary metal (copper), a polyimide and Polyvinylidene fluoride (PVDF). As is known in the art, the characteristic acoustic impedance of a material is given by the product of the density of the material and the velocity of sound in the material.

TABLE I

Material parameters used for design of various examples in Table II

|  | Propagation medium | PZT-5H | Copper | Polyimide | PVDF (for matching) |
|---|---|---|---|---|---|
| Density (kg/m³) | 1000 | 7500 | 8960 | 1454 | 1780 |
| Velocity (m/s) | 1500 | 4800 | 5010 | 2175 | 2100 |

The following Table II compares the two calculated values of specific acoustic impedances $Z_2$, one calculated by a mass and spring model and the other calculated by a rigorous one dimensional model for low and high values (15 and 30 MRayl) of $Z_P$, where the value for the characteristic acoustic impedance of the propagation medium $Z_1$=1.5 MRayl was used. Table II shows that specific acoustic impedance $Z_2$ calculated using the mass and spring model is close enough for actual use.

TABLE II

Examples of designed acoustic impedance converters to match low (~15 MRayl) and high (~30 MRayl) characteristic acoustic impedances of piezoelectric layers, with a propagation medium, such as water or human muscle, having a characteristic acoustic impedance of $Z_R$ = 1.5 MRayl.

| Materials | fo = 1/2π √(K/M) (MHz) | Copper thickness: $t_m$ (μm, $t_m/\lambda$) | Polymer thickness: $t_p$ (μm, $t_p/\lambda$) | $Z_2$, M-K model (MRayl) | $Z_2$ 1-D model (MRayl) |
|---|---|---|---|---|---|
| Cu-polyimide | 2.6 | 32.8, 0.017 | 82, 0.098 | 14.1 | 15.8 |
| Cu-polyimide | 2.6 | 54.4, 0.028 | 54, 0.065 | 28.8 | 30 |
| Cu-polyimide | 5.2 | 16.4, 0.017 | 41, 0.098 | 14.1 | 15.8 |
| Cu-polyimide | 5.2 | 27.2, 0.028 | 27.0, 0.065 | 28.8 | 30 |
| Cu-polyimide | 10.4 | 8.4, 0.017 | 20.5, 0.098 | 14.1 | 15.8 |
| Cu-polyimide | 10.4 | 13.6, 0.028 | 13.5, 0.065 | 28.8 | 30 |
| Cu-PVDF | 5.2 | 14.3, 0.015 | 49, 0.12 | 13.0 | 15.5 |
| Cu-PVDF | 5.2 | 26.3, 0.027 | 31, 0.078 | 28.9 | 30.1 |

As seen in Table II, when the materials and desired specific acoustic impedance are selected, the thickness ratio of polymer layer 130 to metal layer 140 is generally constant for any given frequency. For example, for copper and polyimide, when $Z_2$=30 MRayl is selected, a series of $f_0$=2.6 MHz, 5.2 MHz, and 10.4 MHz gives the same thickness ratio of copper/polyimide ≅1, consistent with Equation (14) above. If a polymer other than polyimide is used, the density and acoustic velocity may differ from that of polyimide, such that the thickness ratio will differ, as may be appreciated from Equation (14) above.

Figure 6:
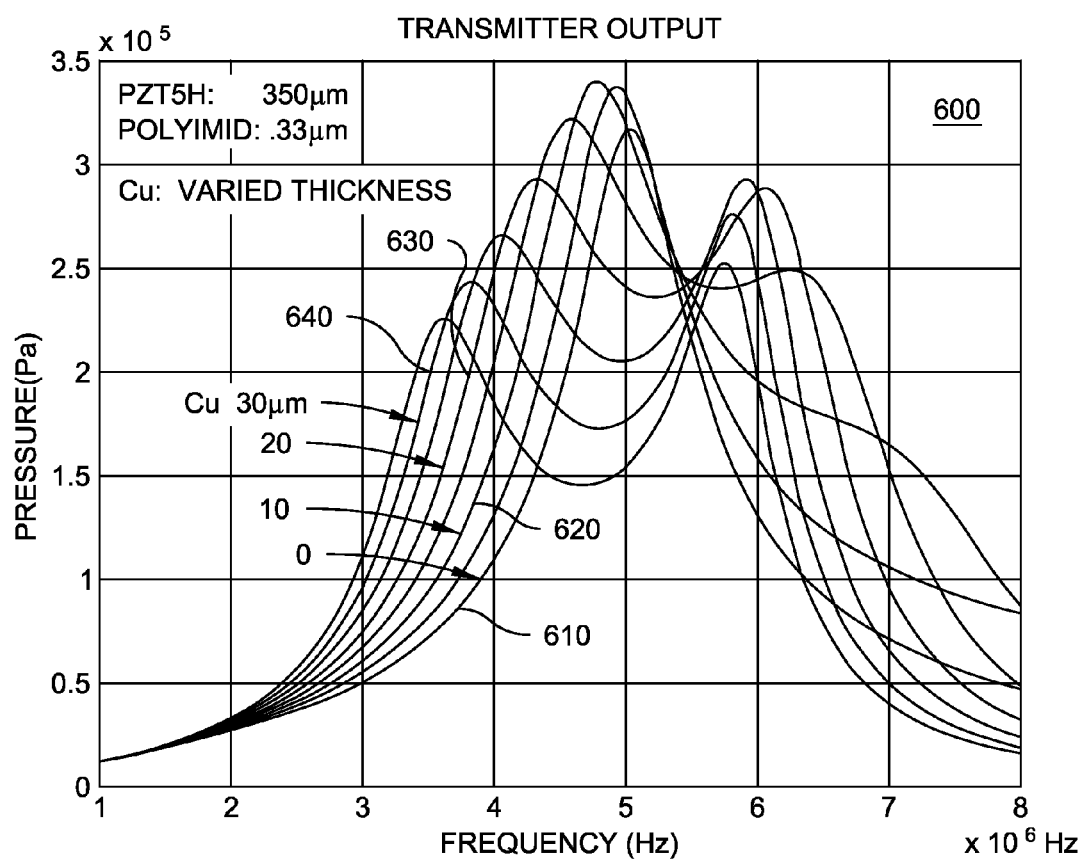
FIG. 6 illustrates a simulated performance of the ultrasonic transducer of FIG. 4, according to an embodiment of the invention.

Referring now to FIG. 6, there is shown a plot 600 of signal strength, represented as pressure as a function of frequency (Hz) for a simulated ultrasonic transducer in transmitter mode, using a one dimensional model (either the Mason model or the KLM model yield effectively the same result). Backing absorber 410 (see FIG. 4 or 5) has a low characteristic acoustic impedance of 4.5 MRayl. Piezoelectric element 110 (see FIG. 4) has a high characteristic acoustic impedance of 30 MRayl; acoustic impedance converter 120 is composed of a polymer layer 130 of 33 µm polyimide and a metal layer 140 of copper with various thicknesses as shown in FIG. 6. The resonant frequency is $f_0 \cong 5.2$ MHz and the thickness of PZT is 350 µm. Curves 610, 620, 630 and 640 represent the signal strength for thicknesses of 0 µm, 10 µm, 20 µm and 30 µm for metal layer 140 of copper. A separate calculation, according to the method described hereinabove, shows that the combination of a 33 µm polyimide polymer layer 130 and a 20 copper metal layer 140 yields an effective characteristic acoustic impedance $Z_C$ of 6.1 MRayl, and 1.5 MRayl of the front propagation medium and is converted to a specific acoustic impedance of 25 MRayl at the front face of PZT layer. This specific acoustic impedance is somewhat lower than the characteristic impedance of PZT. However, for both high sensitivity and wide bandwidth purposes, such a slightly lower impedance at the front face of the PZT layer may be advantageous. For example, FIG. 6 shows curve 630 for 20 µm copper having high sensitivity and wideband and symmetric frequency response, with a center frequency of 5.2 MHz. The structure of 20 µm metal layer 140 of copper and 33 µm polymer layer 130 of polyimide corresponds to a hypothetic material with characteristic acoustic impedance $Z_m = 6.1$ MRayl with one quarter wavelength thickness. If the design is altered to obtain a different designed center frequency $f_o$, the PZT thickness is also different and is inversely proportional to the frequency $f_o$. It will be understood that the thicknesses $t_m$ and $t_p$ are also different for a different center resonant frequency $f_o$. For such a different frequency design, the values of $t_m/\lambda$ and $t_p/\lambda$ may still be kept constant as can be seen in Table II.

FIG. 6 illustrates a simulation of an acoustic output of an ultrasonic transducer 400 (of FIG. 4) acting as a transmitter. The same multilayer acoustic impedance converter structure 120 functions also for an ultrasonic transducer acting as a receiver. The reciprocity principle for an acoustic device generally states that a given structure of a transducer should have the same bandwidth as a receiver as that as a transmitter. Therefore, multilayer acoustic impedance converter 120 described herein may be advantageously used in medical ultrasonic imaging systems. For example, transducer 400 (of FIG. 4) transmits acoustic beams in a short pulse into a human body which beams are then reflected from a target material such as a human organ. The acoustic beams are scanned and the reflections are received by the same transducer 400 (of FIG. 4) and analyzed to reconstruct the image of the human organ, for example, for display on a display device. For such purposes, transducer 400 (FIG. 4) is used as both transmitter and receiver; use of the acoustic impedance converter disclosed herein provides good wideband performance. Metal layer 140 (FIG. 4) serves to transmit ultrasonic energy generated by piezoelectric element 110 (FIG. 4) to propagation medium 150 (FIG. 4) through polymer layer 130 (FIG. 4). Metal layer 140 (FIG. 4) also serves to transmit/receive ultrasonic energy reflected from the target material in propagation medium 150 (FIG. 4) to piezoelectric element 110 (FIG. 4) through polymer layer 130 (FIG. 4).

Figure 7A:
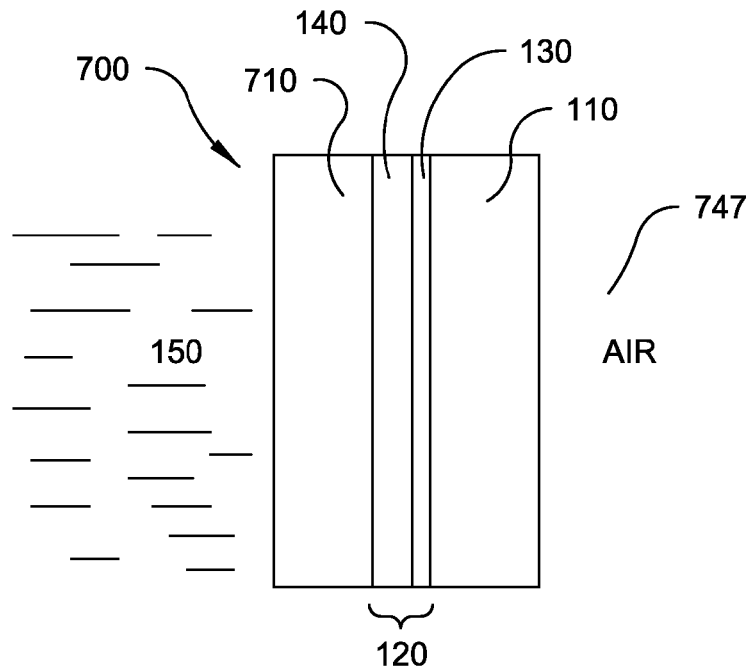
FIG. 7A is a sectional view of an ultrasonic transducer having an impedance converter of the invention, according to an embodiment of the invention.

Referring now to FIG. 7A, another exemplary embodiment of an ultrasonic transducer 700 with acoustic impedance converter 120 according to the invention is illustrated. Ultrasonic transducer 700 has an active piezoelectric element 110 of suitable material, such as PZT. Active piezoelectric element 110 has front and back planar parallel faces. Backing absorber 747 may be formed from any low characteristic acoustic impedance material, such as air, water or an absorber material. Good wideband frequency response may be achieved if acoustic impedance converter 120 is appropriately designed as described herein. Front propagation medium 150 may be water or a human body. Acoustic impedance converter 120 has a polymer layer 130 bonded to the front face of active piezoelectric layer 110, and a metal layer 140 bonded to polymer layer 130. In an exemplary embodiment, both layers 130, 140 are of substantially uniform thicknesses $t_p$, $t_m$ respectively, and these layers function as an impedance converter as already described. The polymer and metal layers are configured so as to have an effective acoustic impedance between that of the piezoelectric material and the propagation medium. The equivalent or effective characteristic acoustic impedance of the multilayer impedance converter 120 is $Z_{C2}$ and the intermediate characteristic acoustic impedance is $Z_{C2} < Z_{PZT}$. Matching layer 710 may be a polymer layer having with a one quarter wavelength thickness and an acoustic impedance $Z_{m1}$ bonded to a front face of acoustic impedance converter 120, for facing propagation medium 150. The characteristic acoustic impedances of the quarter wavelength matching layer 710 and acoustic impedance converter 120 are chosen to satisfy the relationship $Z_1 < Z_{m1} < Z_{C2} < Z_{PZT}$.

Figure 7B:
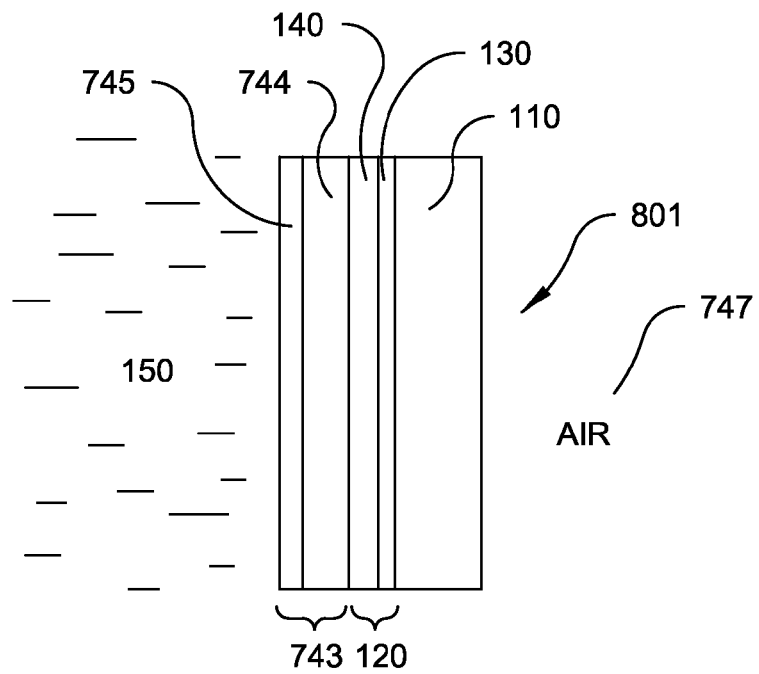
FIG. 7B is a sectional view of an ultrasonic transducer having double matching or impedance converter layers, according to another embodiment of the invention.

Referring now to FIG. 7B, another embodiment of the present invention is illustrated wherein first and second sets of multilayer acoustic impedance converters 120 and 743, respectively, are configured as double matching layers for a transducer 801. Outer acoustic impedance converter 743 is configured according to the structure of multilayer acoustic impedance converter 120 as described herein. A lower characteristic acoustic impedance layer 744 (such as a rubber or latex layer) is bonded to metal layer 140 of inner acoustic impedance converter 120 and a higher characteristic acoustic impedance layer 745 (e.g. a metal, polymer or plastic layer) is adapted to be in contact with propagation medium 150. Outer multilayer acoustic impedance converter 743 functions as a quarter wavelength matching layer 710 as shown in FIG. 7A, and the equivalent characteristic acoustic impedance $Z_{C1}$ and $Z_{C2}$ are so chosen as to satisfy the relationship $Z_1 < Z_{C1} < Z_{C2} < Z_{PZT}$. Inner acoustic impedance converter 120 has a polymer inner layer 130 bonded to piezoelectric element 110, and an outer metal layer 140 bonded to polymer inner layer 130.

Double matching layers have been utilized in prior art ultrasonic transducers using air as a backing absorber. The first layer disposed directly on a PZT element is a quarter wavelength matching layer of material having a high characteristic acoustic impedance, which characteristic acoustic impedance is lower than that of PZT. The second layer is disposed between the first layer and the propagation medium (e.g., water). The high characteristic acoustic impedance material of the first layer in prior art air backing transducers consists of a thin layer of glass (or composite material). The required thickness of such a layer is, for example, 0.52 mm for a transducer having a 2.6 MHz center operating frequency, or 0.26 mm thickness for a transducer having a 5.4 MHz center operating frequency. However, such thin layers of material have proven difficult to manufacture in large scale production systems. The double matching layer apparatus and method as described herein makes it possible to obtain a desired wideband performance that is capable of such large scale manufacturing.

Experimental testing of the embodiment shown in FIG. 7A was accomplished wherein a uniform PZT plate of 0.85 millimeter (mm) thickness with a center operating frequency of 2.6 MHz was used as piezoelectric element 110. Polymer layer 130 comprised a 33 μm PVDF layer. Metal layer 140 comprised a 77 μm layer of brass. It is understood that for such applications the acoustic properties of brass are very similar to those of copper. Matching layer 710 was a 220 μm polyimide layer. The layers were bonded by low viscosity, negligibly thin epoxy bonding layer.

Figure 8:
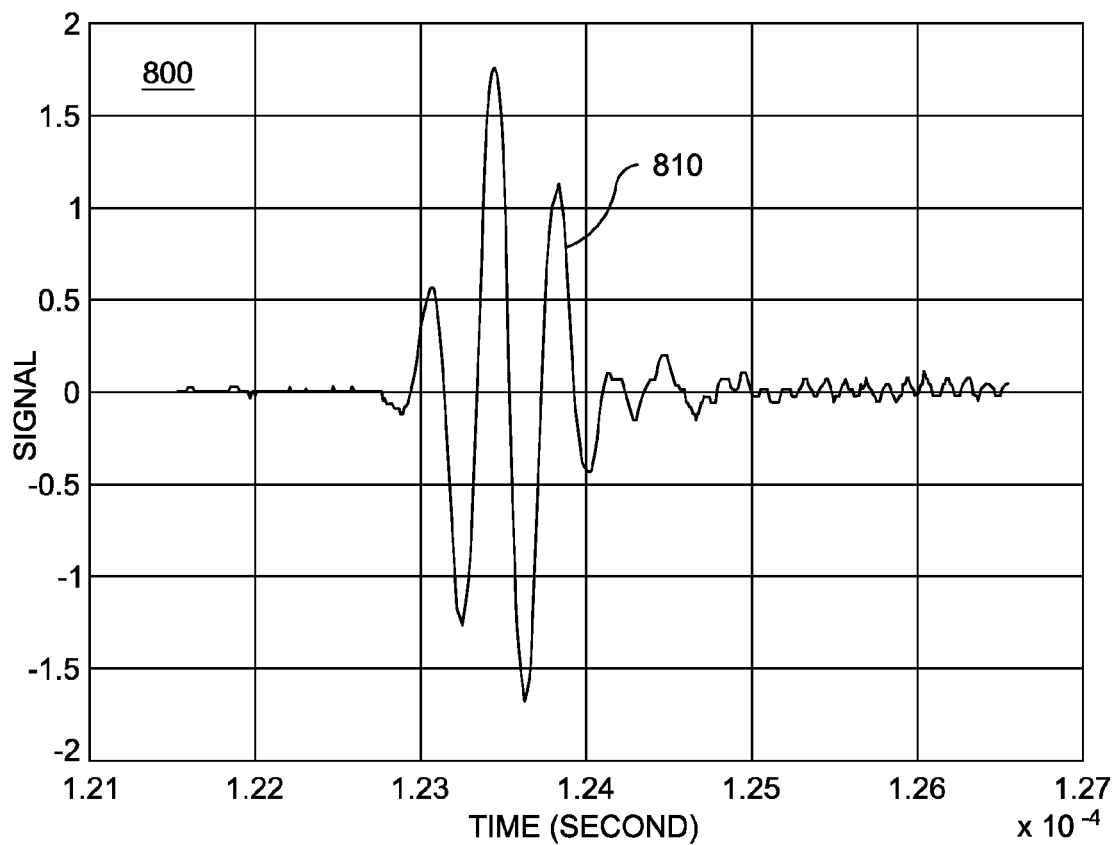
FIG. 8 illustrates an experimental observation of an output waveform as a function of time after a short pulse excitation of an ultrasonic transducer of FIG. 7A.
Figure 9:
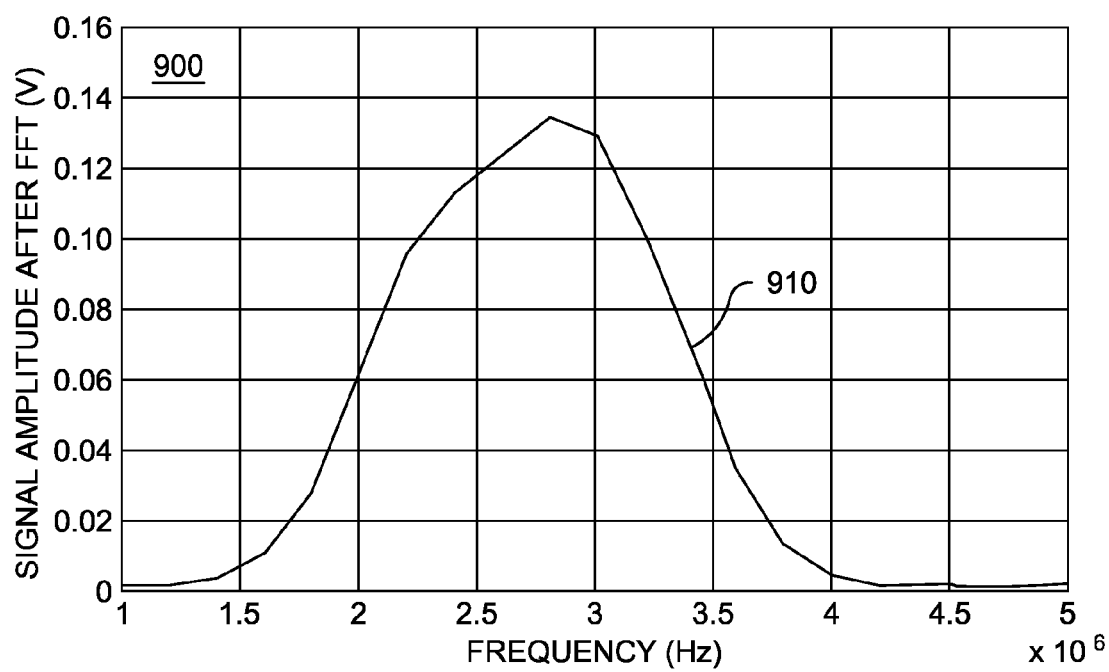
FIG. 9 illustrates a frequency response curve resulting from a Fourier transform of the waveform of FIG. 8.

FIG. 8 shows operational results associated with transducer 700 of FIG. 7A. When the transducer 700 of FIG. 7A is driven by a sharp pulse, the observed waveform 810 is shown in chart 800 of FIG. 8. The frequency performance of the Fourier transformed spectrum 910 of the waveform 810 of FIG. 8 is illustrated in chart 900 of FIG. 9. As can be appreciated from FIG. 8, a sharp pulse waveform 810 is obtained. As can be seen by curve 910 in FIG. 9, wide frequency performance (about 56% relative bandwidth) was achieved.

As previously described, the thicknesses $t_p$ and $t_m$ of polymer layer 130 and metal 140 of acoustic impedance converter 120 may be varied from the values determined using Equations (12) and (13) without departing from the scope of the invention. At a constant center resonant frequency, as the thickness $t_p$ of polymer layer 130 may be increased from the theoretical value obtained using Equation (13), and the thickness $t_m$ of metal layer 140 may be correspondingly decreased from the theoretical value obtained using Equation (12). As the thickness $t_m$ of metal layer 140 approaches zero, the thickness $t_p$ of the polymer layer 130 approaches the thickness of a conventional quarter wavelength matching layer. Thus, as the thickness $t_p$ of polymer layer 130 is decreased from the thickness of a quarter wavelength matching layer, the deviation in the resonance response due to a thinner polymer layer 130 may be compensated by adding metal layer 140 of a given thickness $t_m$. The thickness $t_p$ of polymer layer 130 may be decreased to one-tenth of the theoretical value determined using Equation (13) and still provide adequate transducer performance depending on the requirements of a given application.

It is to be understood that when thicknesses deviate from their original values, the impedances $Z_C$ are different and the function of impedance conversion of the layer pair is likewise different. However, other layers, such as the backing absorber converter and the outermost converter layer (in the case of double layer matching) similarly influence the performance and design these layers to compensate the difference to satisfy overall performance. Thus, in one embodiment, the thickness $t_p$ of polymer layer 130 may range from between about one-tenth of the theoretical value determined using Equation (13) and less than the thickness of a conventional quarter wavelength matching layer for a given center resonant frequency of the transducer. It will be appreciated that alternative embodiments may have thickness $t_p$ of polymer layer 130 about two-tenth, three-tenth, four-tenth, and so on, of the theoretical value determined using Equation (13) and be advantageously employed in different applications requiring different transducer performances. It will further be appreciated that alternative embodiments may also have thicknesses $t_p$ of polymer layer 130 of 1.1, 1.2, 1.3 (etc.) times the theoretical value determined using Equation (13) for different applications.

In other embodiments, only one of the thicknesses $t_p$ and $t_m$ may be varied from the values determined using Equations (12) and (13). For example, the thickness $t_p$ of polymer layer 130 may be half of the theoretical value obtained using Equation (13), without changing the corresponding theoretical thickness $t_m$ of metal layer 140. As will be understood by one skilled in the art, such a combination would result in the resonant frequency of acoustic impedance converter 120 being increased by a factor of approximately the square root of two (2) (i.e., 1.414) from the predetermined center resonant frequency of the transducer. The resulting deformation in the response curve may be useful in other applications of a special frequency response, including but not limited to nondestructive evaluation using ultrasound energy and Doppler flow speed detection.

Variations and modifications to the disclosed embodiments are within the scope of the invention. For example, while the piezoelectric units are generally shown as relatively thin and flat layers, other shapes and forms may be employed. Surfaces that are disclosed as being on and in contact with one another may have interposed therebetween thin layers of materials such as adhesives having little or no effect on the acoustic impedance of the structure.

While the foregoing invention has been described with reference to the above embodiments, various modifications and changes can be made without departing from the spirit of the invention. Accordingly, all such modifications and changes are considered to be within the scope of the appended claims.

What is claimed is:

1. An ultrasonic transducer comprising:
   a piezoelectric element having a characteristic acoustic impedance;
   a front acoustic impedance converter coupled to said piezoelectric element, said front acoustic impedance converter comprising:
      a front polymer layer having a thickness $t_{p1}$ coupled to said piezoelectric element; and
      a front metal layer for transmitting acoustic energy between said front polymer layer and a propagation medium having a characteristic acoustic impedance, said front metal layer having a thickness $t_{m1}$ and being coupled to said front polymer layer on a side of said front polymer layer opposite said piezoelectric element,
   wherein said front polymer layer is arranged intermediate said piezoelectric element and said front metal layer such that there is no contact between said piezoelectric element and said front metal layer.

2. The ultrasonic transducer of claim 1, wherein said characteristic acoustic impedance of said propagation medium is lower than said characteristic acoustic impedance of said piezoelectric element, and wherein said front acoustic impedance converter has an effective characteristic acoustic impedance $Z_c$ between said piezoelectric element and said propagation medium characteristic acoustic impedances.

3. The ultrasonic transducer of claim 2, wherein said thicknesses $t_{m1}$ and $t_{p1}$ are selected based on the densities of said front metal layer and said front polymer layer, said effective characteristic acoustic impedance $Z_c$, a predetermined center resonant frequency of said ultrasonic transducer, and the velocity of sound in said front polymer layer.

4. The ultrasonic transducer of claim 3, wherein said thickness $t_{p1}$ of said front polymer layer is less than one quarter of the wavelength of said predetermined center resonant frequency.

5. The ultrasonic transducer of claim 1, wherein said front polymer layer and said front metal layer comprise discrete continuous layers.

6. The ultrasonic transducer of claim 1, further comprising a backing absorber coupled to said piezoelectric element, said backing absorber having a characteristic acoustic impedance.

7. The ultrasonic transducer of claim 1, further comprising a quarter wavelength matching layer configured to be in contact with said propagation medium, said quarter wavelength matching layer coupled to said front metal layer.

8. The ultrasonic transducer of claim 1, further comprising a low characteristic acoustic impedance layer coupled to said front metal layer, and a high characteristic acoustic impedance layer coupled to said low characteristic acoustic impedance layer for being in contact with said propagation medium.

9. The ultrasonic transducer of claim 1, wherein said front polymer layer is arranged continuously between said piezoelectric element and said front metal layer.

10. An ultrasonic transducer comprising:
a piezoelectric element having a characteristic acoustic impedance;
a front acoustic impedance converter coupled to said piezoelectric element, said front acoustic impedance converter comprising:
a front polymer layer having a thickness $t_{p1}$ coupled to said piezoelectric element; and
a front metal layer for transmitting acoustic energy between said front polymer layer and a propagation medium having a characteristic acoustic impedance, said front metal layer having a thickness $t_{m1}$ and being coupled to said front polymer layer,
a backing absorber coupled to said piezoelectric element, said backing absorber having a characteristic acoustic impedance, and
a back acoustic impedance converter interposed between said backing absorber and said piezoelectric element,
wherein said back acoustic impedance converter comprises:
a back polymer layer having a thickness $t_{p2}$ and having first and second surfaces; and
a back metal shielding layer having a thickness $t_{m2}$ and having first and second surfaces, said first surface of said back metal shielding layer coupled to said second surface of said back polymer layer, and said second surface of said back metal shielding layer coupled to said backing absorber.

11. The ultrasonic transducer of claim 10, wherein said characteristic acoustic impedance of said propagation medium is lower than said characteristic acoustic impedance of said piezoelectric element.

12. The ultrasonic transducer of claim 11, wherein said front acoustic impedance converter has an effective characteristic acoustic impedance $Z_c$ between said piezoelectric element and said propagation medium characteristic acoustic impedances.

13. The ultrasonic transducer of claim 10, wherein said front acoustic impedance converter has a resonant frequency, and said back acoustic impedance converter has a resonant frequency,
wherein said resonant frequency of the front acoustic impedance converter is higher than a predetermined center resonant frequency of the ultrasonic transducer, and
wherein said resonant frequency of the back acoustic impedance converter is lower than the predetermined center resonant frequency of the ultrasonic transducer.

14. The ultrasonic transducer of claim 10, wherein said front acoustic impedance converter has a resonant frequency, and said back acoustic impedance converter has a resonant frequency,
wherein said resonant frequency of the front acoustic impedance converter is lower than a predetermined center resonant frequency of the ultrasonic transducer, and
wherein said resonant frequency of the back acoustic impedance converter is higher than the predetermined center resonant frequency of the ultrasonic transducer.

15. An ultrasonic transducer comprising:
a piezoelectric element having a characteristic acoustic impedance;
a front acoustic impedance converter coupled to said piezoelectric element, said front acoustic impedance converter comprising:
a front polymer layer having a thickness $t_{p1}$ coupled to said piezoelectric element; and
a front metal layer for transmitting acoustic energy between said front polymer layer and a propagation medium having a characteristic acoustic impedance, said front metal layer having a thickness $t_{m1}$ and being coupled to said front polymer layer on a side of said front polymer layer opposite said piezoelectric element,
wherein said front polymer layer completely isolates said front metal layer from said piezoelectric element.

16. The ultrasonic transducer of claim 15, wherein said characteristic acoustic impedance of said propagation medium is lower than said characteristic acoustic impedance of said piezoelectric element, and wherein said front acoustic impedance converter has an effective characteristic acoustic impedance $Z_c$ between said piezoelectric element and said propagation medium characteristic acoustic impedances.

17. The ultrasonic transducer of claim 16, wherein said thicknesses $t_{m1}$ and $t_{p1}$ are selected based on the densities of said front metal layer and said front polymer layer, said effective characteristic acoustic impedance $Z_c$, a predetermined center resonant frequency of said ultrasonic transducer, and the velocity of sound in said front polymer layer.

18. The ultrasonic transducer of claim 17, wherein said thickness $t_{p1}$ of said front polymer layer is less than one quarter of the wavelength of said predetermined center resonant frequency.

19. The ultrasonic transducer of claim 15, further comprising a backing absorber coupled to said piezoelectric element, said backing absorber having a characteristic acoustic impedance.

20. The ultrasonic transducer of claim 15, further comprising a low characteristic acoustic impedance layer coupled to said front metal layer, and a high characteristic acoustic impedance layer coupled to said low characteristic acoustic impedance layer for being in contact with said propagation medium.

* * * * *